United States Patent
Hillebrand et al.

(10) Patent No.: US 6,469,216 B2
(45) Date of Patent: Oct. 22, 2002

(54) PROCESS FOR HYDROFORMYLATION USING A CATALYST BASED ON COBALT AND/OR RHODIUM EMPLOYED IN A TWO-PHASE MEDIUM

(75) Inventors: Gerhard Hillebrand, Rueil Malmaison; André Hirschauer, Montesson; Dominique Commereuc, Meudon; Hélène Olivier-Bourbigou, Rueil Malmaison; Lucien Saussine, Croissy sur seine, all of (FR)

(73) Assignee: Institut Francais du Petrole, Rueil-Malmaisson Cedex (FR)

( * ) Notice: Subject to any disclaimer, the term of this patent is extended or adjusted under 35 U.S.C. 154(b) by 0 days.

(21) Appl. No.: 09/730,795

(22) Filed: Dec. 7, 2000

(65) Prior Publication Data

US 2001/0039363 A1 Nov. 8, 2001

(30) Foreign Application Priority Data

Dec. 8, 1999 (FR) .......................................... 99 15573

(51) Int. Cl.$^7$ .............................................. C07C 45/50
(52) U.S. Cl. ...................................... 568/454; 568/451
(58) Field of Search ................................. 568/451, 454

(56) References Cited

U.S. PATENT DOCUMENTS 5,874,638 A * 2/1999 Chauvin et al. ............ 568/454

FOREIGN PATENT DOCUMENTS

| EP | 0 107 430 | 5/1984 |
|---|---|---|
| EP | 0 776 880 | 6/1997 |
| EP | 0 924 182 | 6/1999 |

* cited by examiner

Primary Examiner—Sreeni Padmanabhan
(74) Attorney, Agent, or Firm—Millen, White, Zelano & Branigan, P.C.

(57) ABSTRACT

In an improved process for hydroformylation of olefinically unsaturated compounds using a catalyst based on cobalt and/or rhodium employed in a two-phase medium, a catalyst based on cobalt and/or rhodium is used dissolved in a non-aqueous ionic solvent which is liquid at a temperature of less than 90° C., in which the aldehydes formed are slightly soluble or insoluble. More particularly, the catalyst comprises at least one complex of cobalt and/or rhodium co-ordinated with at least one nitrogen-containing ligand and the non-aqueous ionic solvent comprises at least one quaternary ammonium and/or phosphonium cation and at least one inorganic anion. At the end of the reaction, the organic phase is generally separated and the ionic non-aqueous solvent phase containing the catalyst can be re-used.

27 Claims, No Drawings

PROCESS FOR HYDROFORMYLATION USING A CATALYST BASED ON COBALT AND/OR RHODIUM EMPLOYED IN A TWO-PHASE MEDIUM

BACKGROUND OF THE INVENTION

1. Field of the Invention

The present invention relates to an improved process for hydroformylation of olefinically unsaturated compounds employing a catalyst based on cobalt and/or rhodium used in a two-phase medium. The catalyst based on cobalt and/or rhodium, which comprises at least one cobalt and/or rhodium complex co-ordinated with at least one nitrogen-containing ligand, is dissolved in a non-aqueous ionic solvent which is liquid at a temperature of less than 90° C., in which the aldehydes formed are slightly soluble or insoluble.

Hydroformylation of olefinic compounds is a reaction of major industrial importance and the majority of processes use homogeneous catalysts dissolved in an organic phase constituted by the reactants, products and possibly excess ligand, although difficulties are encountered in separating and recovering the catalyst, in particular when it is used in relatively large quantities, as is the case with catalysts based on cobalt or on a noble metal, as is the case with rhodium-based catalysts.

2. Description of the Prior Art

One solution aimed at solving that problem has been developed by Bartik et al., Organometallics (1993), 12, 164–170, J. Organometal. Chem. (1994), 480, 15–21, and by Beller et al., J. molecular Catal. A: Chemical (1999), 143, 31–39. It consists of carrying out hydroformylation in the presence of an aqueous solution containing a cobalt complex which is rendered water-soluble by the presence of a phosphine-sulfonate ligand such as the sodium salt of trisulfonated triphenylphosphine or a trisulfonated tris-(alkylphenyl)phosphine. International Patent Application WO 97/00132 describes cobalt clusters substituted by trialkoxysilylmethyl groups which render them water-soluble. In that manner, the organic phase containing the aldehydes is readily separated from the aqueous phase containing the catalyst.

A further solution aimed at solving that problem has been described in French Patent No. 2 314 910. It consists of carrying out hydroformylation in the presence of an aqueous solution containing a rhodium complex which is rendered water-soluble by the presence of a sulfonated phosphine ligand which is itself water-soluble, such as the sodium salt of trisulfonated triphenylphosphine. In that manner, the organic phase containing the aldehydes is readily separated from the aqueous phase containing the catalyst. That technique has been studied widely and those studies have been discussed in an article by W. A. Herrmann in "Angewandte Chemie International", 1993, volume 32, pages 1524 ff.

Despite the huge industrial importance of such techniques for hydroformylation of propylene, such two-phase systems suffer from a lack of solubility of olefins in water, leading to relatively low reaction rates, which render them unsuitable for long chain olefins.

U.S. Pat. No. 3,565,823 describes a technique consisting of dispersing a transition metal compound in a quaternary ammonium or phosphonium salt of tin or germanium with formula $(R^1R^2R^3R^4Z)YX_3$ where $R^1$, $R^2$, $R^3$, and $R^4$ are hydrocarbyl residues containing up to 18 carbon atoms, Z is nitrogen or phosphorous, Y is tin or germanium and X is a halogen, for example chlorine or bromine.

U.S. Pat. No. 3,832,391 claims a process for olefin carbonylation using the same composition. The above compositions have the disadvantage of having a relatively high melting point, for example over 90° C., which complicates manipulation of the catalyst solutions and the reaction products.

Assignee's U.S. Pat. No. 5,874,638 describes that it is possible to benefit both from the advantages of a two-phase operation while avoiding the disadvantages linked to using water and to using compounds with a high melting point, by dissolving certain catalytic compounds of transition metals from groups 8, 9 and 10, known to catalyze hydroformylation, in non-aqueous ionic solvents which are constituted by organic-inorganic salts which are liquid at ambient temperature. This patent on column 3, lines 25–50 states as follows, with respect to the organic ligand associated or complexed with the transition metals:

Organic ligands such as tertiary phosphines, stibines and arsines, phosphites, and in particular arylphosphites can advantageously be associated with all these compounds. They can be mono- or bidentate. These ligands can carry at least one other function such as an amine, ammonium, alcohol, carboxylic acid or sulphonate on the heteroatom and/or on the carbon chain. Examples are triphenylphosphine, triphenylphosphite, trimethylphosphite, the sodium salt of monosulphonated triphenylphosphine, and the sodium salt of monosulphonated triphenylphosphine, and the sodium salt of monosulphonated triphenylphosphine. The choice of transition metal catalytic compound is not critical. Examples are $HRh(CO)(PR_3)_3$, $HRh(CO)_2(PR_3)$, $HRh(CO)[P(OR)_3]_3$, $Rh(acac)(CO)_2$, (acac represents acetylaccetonate), $Rh_6(CO)_{16}$, $[Rh(norbonadiene)(PPh_3)_2]^+[PF_6]^-$, $[Rh(CO)_3(PPh_3)_2]^+[BPh_4]^-$, $Rhcl(CO)(PEt_3)_2$, $[RhCl(cyclooctadiene)]_2$, $[Rh(CO)_3(PR_3)_2]^+BPh_4^1$, $[Rh(CO)_3(PR_3)_2]^+PF_6^-, HCo(CO)_4$, $Ru_3(CO)_{12}$, $[RuH(CO)(acetonitrile)_2(PPh_3)_3]^+[BF_4]^-$, $PtCl_2$(cyclooctadiene), $[Ir(CO)_3(PPh_3)]^+[PF_6]^-$, $[HPt(PEt_3)_3]^+[PF_6]$, where R is a hydrocarbyl radical, for example alkyl, cycloalkyl, aryl, which may or may not be substituted. Completely inorganic salts may also be used, such as $Rh_2O_3$, $Pd(NO_3)_2$ and $Rh(NO_3)_3$, also halides such as $RHCl_3$, $3H_2O$, although halides are not preferred. The transition metal compound and/or the ligand can also be already dissolved in an organic solvent.

SUMMARY OF THE INVENTION

It has now been discovered that the activity and selectivity for the hydroformylation reaction of catalysts based on cobalt and/or rhodium used in an ionic non-aqueous solvent which is liquid at a temperature of less than 90° C. are greatly improved by using nitrogen-containing ligand to complex the cobalt and/or rhodium.

More precisely, the invention provides a process for hydroformylation in the liquid phase of olefinically unsaturated compounds in which the reaction is carried out in the presence of at least one complex of cobalt and/or rhodium co-ordinated by at least one nitrogen-containing ligand, and of at least one non-aqueous ionic solvent comprising at least one organic-inorganic salt with general formula $Q^+A^-$, where $Q^+$ represents a quaternary ammonium and/or quaternary phosphonium cation and $A^-$ represents an anion.

The cobalt and/or rhodium precursor compounds of the catalyst are selected from the group formed by cobalt and/or rhodium salts such as acetylacetonates, carboxylates, in particular formate or acetate, and carbonyl complexes, such as dicobalt-octacarbonyl, cobalt-tetracarbonyl hydride, rhodium-dicarbonyl acetylacetonate and carbonyl clusters. The choice of the cobalt and/or rhodium precursor compound is not critical, but in general it is preferable to avoid halides.

The nitrogen-containing ligand is preferably selected from the group formed by monoamines, di-, tri- and polyamines, imines, diimines, pyridine and substituted pyridines, bipyridine, imidazole and substituted imidazoles, pyrrole and substituted pyrroles, pyrazole and substituted pyrazoles. Non limiting examples which can be cited are triethylamine, ethylene diamine, tetramethylethylenediamine, diethylenetriamine, diazabicyclooctane, 1,4,7-trimethyl-1,4,7-triazacyclononane, N,N'-dimethyl-ethane-1,2-diimine, N,N'-di-tert-butyl-ethane-1,2-diimine, N,N'-di-t-butyl-butane-2,3-diimine, N,N'-diphenyl-ethane-1,2-diimine, N,N'-bis-(2,6-dimethylphenyl)-ethane-1,2-diimine, N,N'-bis-(2,6-diisopropyl-phenyl)-ethane-1,2-diimine, N,N'-bis-(2,6-di-t-butyl-phenyl)-ethane-1,2-diimine, N,N'-diphenyl-butane-2,3-diimine, N,N'-bis-(2,6-dimethyl-phenyl)-butane-2,3-diimine, N,N'-bis-(2,6-diisopropyl-phenyl)-butane-2,3-diimine, N,N'-bis-(di-t-butyl-2,6-phenyl)-butane-2,3-diimine, pyridine, picolines, t-butylpyridine, bipyridine, di-t-butyl-bipyridine, imidazole, N-methylimidazole, N-butylimidazole, benzimidazole, pyrrole, N-methylpyrrole and 2,6-dimethyl-pyrrole.

The nitrogen-containing ligand can also include other organic functions, such as alcohol, aldehyde, ketone, carboxylic acid, ester, nitrile, quaternary ammonium and/or phosphonium, also sulfonium functions. Non limiting examples which can be cited are picolinic acids and esters, 2,6 dialkoxypyridines, salicylaldimines, 2,6-bis-N-aryliminopyridines, 1-dialkyl (and diaryl) phosphino-2-(4-pyridyl)ethanes, alkyl 2-(4-pyridyl)-acetates, alkyl 2-(2-pyridyl)-acetates, ethylene glycol bis-3-(4-pyridyl)-propanoate, 2-(2-pyridyl)-ethanol, 3-(2-pyridyl)-propanol and 3-(2-pyridyl)-propyl acetate.

The non-aqueous ionic solvent is selected from the group formed by liquid salts with general formula $Q^+A^-$ where $Q^+$ represents quaternary ammonium and/or quaternary phosphonium and $A^-$ represents any anion which can form a liquid salt at low temperature, i.e., below 90° C. and advantageously at most 85° C., preferably below 50° C. Preferred anions $A^-$ are acetate, halogenoacetate, tetrafluoroborate, tetrachloroborate, hexafluorophosphate, hexafluoroantimonate, fluorosulfonate, perfluoroalkylsulfonate, bis-(perfluoroalkylsulfonyl)amide and arene-sulfonate ions.

The quaternary ammonium and/or phosphonium ions preferably have general formula $NR^1R^2R^3R^{4+}$ and $PR^1R^2R^3R^{4+}$ or general formula $R^1R^2N=C\ R^3R^{4+}$ or $R^1R^2P=CR^3R^{4+}$, where $R^1R^2$, $R^3$, and $R^4$, which may be identical or different, represent hydrogen (with the exception of the $NH_4^+$ cation for $NR^1R^2R^3R^{4+}$), preferably a single substituent representing hydrogen, or hydrocarbyl residues containing 1 to 12 carbon atoms, for example saturated or unsaturated alkyl, cycloalkyl or aromatic generals, aryl or aralkyl groups containing 1 to 12 carbon atoms. The ammonium and/or phosphonium can also be a derivative of nitrogen-containing and/or phosphorus-containing heterocycles containing 1, 2 or 3 nitrogen and/or phosphorus atoms, in which the cycles are constituted by 4 to 10 atoms, preferably 5 to 6 atoms.

The quaternary ammonium and/or phosphonium can also be a cation with formula:

$R^1R^{2+}N=CR^3-R^5-R^3C=N^+R^1R^2$ and/or $R^1R^{2+}P=CR^3-R^5-R^3C=P^{+R1}R^2$ where $R^1$, $R^2$ and $R^3$, which may be identical or different, are defined as above, and $R^5$ represents an alkylene or phenylene residue. Examples of groups $R^1$, $R^2$, $R^3$, and $R^4$ which can be mentioned include the following radicals: methyl, ethyl, propyl, isopropyl, butyl, secondary butyl, tertiary butyl, amyl, methylene, ethylidiene, phenyl or benzyl; $R^5$ can be a methylene, ethylene, propylene or phenylene group. The ammonium and/or phosphonium cation is preferably selected from the group formed by N-butylpyridinium, N-ethylpyridinium, 3-ethyl-1-methylimidazolium, 3-butyl-1 methylimidazolium, diethylpyrazolium, pyridinium, trimethylphenyl ammonium and tetrabutyl-phosphonium. Examples of salts which can be used in the invention which can be cited are N-butylpyridnium hexafluorophosphate, N-ethylpyridinium tetrafluoroborate, tetrabutylphosphonium tetrafluoroborate, 3-butyl-1-methylimidazolium tetrafluoroborate, 3-butyl-1-methylimidazolium hexafluoroantimonate, 3-butyl-1-methylimidazolium hexafluorophosphate, 3-butyl-1-methylimidazolium trifluoromethylsulfonate, pyridinium fluorosulfonate and trimethylphenylammonium hexafluorophosphate. These salts can be used alone or as a mixture.

The catalytic composition is obtained by mixing the liquid salt with the cobalt and/or rhodium compound and the nitrogen-containing ligand in any known manner. It is also possible to first dissolve the transition metal compound (cobalt and/or rhodium) and/or the ligand in the organic solvent.

The complex between the cobalt and/or rhodium precursor and the nitrogen-containing ligand can be prepared prior to the reaction by mixing the cobalt and/or rhodium precursor with the ligand in a suitable solvent, for example an organic solvent or the non-aqueous ionic solvent which will then by used in the catalytic reaction. The complex can also be prepared in situ by mixing the cobalt and/or rhodium precursor and the nitrogen-containing ligand directly in the hydroformylation reactor.

In general, the catalytic composition can contain a miscible or partially miscible organic solvent such as an aromatic hydrocarbon, and/or a non-miscible aliphatic hydrocarbon which enables better phase separation. Preferably, the catalytic composition contains no water.

The concentration of cobalt and/or rhodium complex in the ionic liquid "molten salt" is not critical. It is advantageously in the range 0.1 moles per liter of "molten salt" to 5 moles per liter, preferably in the range 1 mole to 1 mole per liter, still more preferably in the range 100 to 500 moles per liter. The mole ratio between the nitrogen-containing ligand and the cobalt and/or rhodium compound is in the range 0.1 to 100, preferably in the range 1 to 20.

The components in the composition of the invention can be mixed in any order at a temperature in the range −20° C. to 200° C., preferably in the range 0° C. to 140° C., and advantageously in the range 20° C. to 90° C.

Olefinically unsaturated compounds which can be hydroformylated are selected from the group formed by monoolefins, diolefins, in particular conjugated diolefins and olefinic compounds comprising one or more heteroatoms, in particular unsaturated compounds such as compounds with a ketone function or a carboxylic acid function. Examples which can be cited are hydroformylation of pentenes to hexanal and methylpentanal, hexenes to isoheptanals, isooctenes to isononanals. These olefinic compounds can be used pure or diluted with saturated or unsaturated hydrocarbons.

The ratio of the partial pressures of hydrogen to carbon monoxide used in the reaction medium for hydroformylation can be 10:1 to 1:10, preferably in a ratio of 1:1, but any other ratio can be used depending on the implementation of the process.

The temperature at which hydroformylation is carried out is in the range 30° C. to 200° C.; advantageously the temperature is less than 150° C., preferably in the range 50° C. to less than 150° C. The pressure can be in the range 1 MPa to 20 MPa, preferably in the range 2 MPa to 15 MPa.

Catalytic hydroformylation of the unsaturated compounds can be carried out in a closed system, in a semi-open system or continuously with one or more reaction stages. At the reactor outlet, the organic phase containing the reaction products is advantageously separated by simple decantation of the ionic solvent phase containing the "molten salt" and the major portion of the catalyst. This ionic solvent phase, which contains at least a portion of the catalyst, is at least partially returned to the reactor, the other portion optionally being treated to eliminate the catalyst residues.

The entire disclosure of all applications, patents and publications, cited above and below, and of corresponding French application 99/15573, filed Dec. 8, 1999, are hereby incorporated by reference.

The following examples illustrate the invention without limiting its scope.

EXAMPLE 1

The hydroformylation reaction was carried out in a 300 ml volume stainless steel reactor provided with a double envelope to regulate the temperature by circulating a heat exchange fluid, and provided with an efficient stirring means with counteracting blades. 0.4 g of dicobalt-octacarbonyl (i.e., 2.3 millimoles of cobalt), 0.16 g of pyridine (2 millimoles), 10 ml of butyl-methyl-imidazolium tetrafluoroborate, 30 ml of heptane and 30 ml of hexene-1 were introduced into this autoclave, which had first been purged of air and moisture and placed under a mixture of hydrogen and carbon monoxide (1/1 molar) at atmospheric pressure. The pressure of the hydrogen-carbon monoxide mixture (1/1 molar) was brought to 10 MPa, the temperature was increased to 125° C. and stirring was commenced. After 6 hours, stirring was stopped and the reaction mixture was allowed to cool and decant, then the pressure was released. After extraction from the autoclave, the upper organic phase was slightly colored. The hexene-1 conversion was 98.9% by weight. The selectivity for C7 aldehydes was 88.9% and the n/iso (n-heptanal/isoheptanals) ratio was 1.9.

EXAMPLE 2

The hydroformylation reaction was carried out in the same apparatus and using the same operating procedure as that described in Example 1. 0.4 g of dicobalt-octacarbonyl (i.e., 2.3 millimoles of cobalt), 0.16 g of pyridine (2 millimoles), 10 ml of butyl-methyl-imidazolium tetrafluoroborate, 30 ml of heptane and 30 ml of a C6 olefin cut containing 7.4% of 2,3-dimethyl-butene-1, 12.1% of 2,3-dimethyl-butene-2, 23.5% of 2-methyl-pentene-1 and 57% of 2-methyl-pentene-2 was introduced. The pressure of the hydrogen-carbon monoxide mixture (1/1 molar) was brought to 12 MPa, the temperature was increased to 90° C. and stirring was commenced. After 6 hours, stirring was stopped and the reaction mixture was allowed to cool and decant, then the pressure was released. After extraction from the autoclave, the upper organic phase was slightly colored. The C6 olefin conversion was 66% by weight. The selectivity for C7 aldehydes was 60%. The other products were hexanes (18%) and heavy products.

EXAMPLE 3

The hydroformylation reaction was carried out in the same apparatus and using the same operating procedure as that described in Example 1. 0.35 g of dicobalt-octacarbonyl (i.e., 2 millimoles of cobalt). 0.28 g of 1-dicyclopentyl-2-phosphino-(4-pyridyl)-ethane (1 millimole), 10 ml of butyl-methyl-imidazolium tetrafluoroborate, 10 ml of heptane and 30 ml of hexene-1 were introduced. The pressure of the hydrogen-carbon monoxide mixture (1/1 molar) was brought to 11 MPa, the temperature was increased to 140° C. and stirring was commenced. After 6 hours, stirring was stopped and the reaction mixture was allowed to cool and decant, then the pressure was released. After extraction from the autoclave, the upper organic phase was very slightly colored. The hexene-1 conversion was 83.8% by weight. The selectivity for C7 aldehydes was 52.8% and the n/iso (n-heptanal/isoheptanals) ratio was 1.6. The other products were hexene-2 and hexene-3 (11%) and heavy products.

EXAMPLE 4

The hydroformylation reaction was carried out in the same apparatus and using the same operating procedure as that described in Example 1. 1.6 g of dicobalt-octacarbonyl (i.e., 9.3 millimoles of cobalt), 3.3 g of ethylene glycol bis-3-(4-pyridyl)-propanoate (10 millimoles), 10 ml of butyl-methyl-imidazolium tetrafluoroborate, 30 ml of heptane and 30 ml of hexene-1 were introduced. The pressure of the hydrogen-carbon monoxide mixture (1/1 molar) was brought to 9.5 MPa, the temperature was increased to 95° C. and stirring was commenced. After 6 hours, stirring was stopped and the reaction mixture was allowed to cool and decant, then the pressure was released. After extraction from the autoclave, the upper organic phase was practically colorless. The hexene-1 conversion was 65% by weight. The selectivity for C7 aldehydes was 67% and the n/iso (n-heptanal/isoheptanals) ratio was 4.2. The other products were C7 alcohols (11%) and heavy products.

EXAMPLE 5

The hydroformylation reaction was carried out in the same apparatus and using the same operating procedure as that described in Example 1. 1.6 g of dicobalt-octacarbonyl (i.e., 9.3 millimoles of cobalt), 3.3 g of bis-3-(4-pyridyl)-propanoate ethylene glycol (2.4 millimoles), 10 ml of butyl-methyl-imidazolium tetrafluoroborate, 30 ml of heptane and 30 ml of hexene-1 were introduced. The pressure of the hydrogen-carbon monoxide mixture (1/1 molar) was brought to 8 MPa, the temperature was increased to 80° C. and stirring was commenced. After 6 hours, stirring was stopped and the reaction mixture was allowed to cool and decant, then the pressure was released. After extraction from the autoclave, the upper organic phase was slightly colored. The hexene-1 conversion was 68% by weight. The selectivity for C7 aldehydes was 90% and the n/iso (n-heptanal/isoheptanals) ratio was 3.9.

EXAMPLE 6

The hydroformylation reaction was carried out in the same apparatus and using the same operating procedure as that described in Example 1. 0.4 g of dicobalt-octacarbonyl (i.e., 2.3 millimoles of cobalt), 0.6 g of 3-(2-pyridyl)-propanol (4.4 millimoles), 0.75 ml of butyl-methylimid tetrafluoroborate, 30 ml of heptane and 30 ml of hexene-1 were introduced. The pressure of the hydrogen-carbon monoxide mixture (1/1 molar) was brought to 6.5 MPa, the temperature was increased to 95° C. and stirring was commenced. After 6 hours, stirring was stopped and the reaction mixture was allowed to cool and decant, then the pressure was released. After extraction from the autoclave, the upper organic phase was slightly colored. The hexene-1 conversion was 58% by weight. The selectivity for C7 aldehydes was 92.8% and the n/iso (n-heptanal/isoheptanals)ratio was 3.9.

EXAMPLE 7

The hydroformylation reaction was carried out in the same apparatus and using the same operating procedure as that described in Example 1. 0.4 g of dicobalt-octacarbonyl (i.e., 2.3 millimoles of cobalt), 0.72 g of 3-(2-pyridyl)-propyl acetate (4 millimoles), 9 ml of butyl-methyl-imidazolium bis-(trifluoromethylsulfonyl) amide, 30 ml of heptane and 30 ml of hexene-1 were introduced. The pressure of the hydrogen-carbon monoxide mixture (1/1 molar) was brought to 9 MPa, the temperature was increased to 95° C. and stirring was commenced. After 6 hours, stirring was stopped and the reaction mixture was allowed to cool and decant, then the pressure was released. After extraction from the autoclave, the upper organic phase was slightly yellow in color. The hexene-1 conversion was 86% by weight. The selectivity for C7 aldehydes was 84.6% and the n/iso (n-heptanal/isoheptanals) ratio was 2.8.

EXAMPLE 8

The hydroformylation reaction was carried out in the same apparatus and using the same operating procedure as that described in Example 1. 0.4 g of dicobalt-octacarbonyl (i.e., 2.3 millimoles of cobalt), 0.8 g of N,N'-bis-(2,6-diisopropylphenyl)-butane-2,3-diimine (2 millimoles), 6 ml of butyl-methyl-imidazolium tetrafluoroborate, 30 ml of heptane and 30 ml of hexene-1 were introduced. The pressure of the hydrogen-carbon monoxide mixture (1/1 molar) was brought to 9.4 MPa, the temperature was increased to 90° C. and stirring was commenced. After 6 hours, stirring was stopped and the reaction mixture was allowed to cool and decant, then the pressure was released. After extraction from the autoclave, the upper organic phase was slightly colored. The hexene-1 conversion was 95.5% by weight. The selectivity for C7 aldehydes was 89.3% and the n/iso (n-heptanal/isoheptanals) ratio was 3.

EXAMPLE 9

The hydroformylation reaction was carried out in the same apparatus and using the same operating procedure as that described in Example 1. 0.4 g of dicobalt-octacarbonyl (i.e., 2.3 millimoles of cobalt), 0.72 g of 3-(2-pyridyl)-propyl acetate (4 millimoles), 6 ml of tetra-(hexyloctyl)-phosphonium tetrafluoroborate, 30 ml of heptane and 30 ml of hexene-1 were introduced. The pressure of the hydrogen-carbon monoxide mixture (1/1 molar) was brought to 8.1 MPa, the temperature was increased to 95° C. and stirring was commenced. After 6 hours, stirring was stopped and the reaction mixture was allowed to cool and decant, then the pressure was released. After extraction from the autoclave, the upper organic phase was slightly colored. The hexene-1 conversion was 57% by weight. The selectivity for C7 aldehydes was 80% and the n/iso (n-heptanal/isoheptanals) ratio was 2.4.

EXAMPLE 10 (comparative)

The hydroformylation reaction was carried out in the same apparatus and using the same operating procedure as that described in Example 1. 0.35 g of dicobalt-octacarbonyl (i.e., 2 millimoles of cobalt), 0.5 g of tri-n-butylphosphine (2.5 millimoles), 10 ml of butyl-methyl-imidazolium tetrafluoroborate, 10 ml of heptane and 30 ml of hexene-1 were introduced. The pressure of the hydrogen-carbon monoxide mixture (1/1 molar) was brought to 10 MPa, the temperature was increased to 125° C. and stirring was commenced. After 6 hours, stirring was stopped and the reaction mixture was allowed to cool and decant, then the pressure was released. After extraction from the autoclave, the upper organic phase was slightly colored. The hexene-1 conversion was 21% by weight. The selectivity for C7 aldehydes was 34% and the n/iso(n-heptanal/isoheptanals) ratio was 2.7. Comparison with Example 1 shows the beneficial effect of a nitrogen-containing ligand over the phosphorous-containing ligands of the prior art.

EXAMPLE 11

The hydroformylation reaction was carried out in the same apparatus and using the same operating procedure as that described in Example 1. 19.3 mg of rhodium-dicarbonyl acetylacetonate, 30.3 mg of N,N'-bis-(2,6-diisopropylphenyl)-butane-2,3-diimine, 5 g of tributyl-tetradecylphosphonium tetrafluoroborate, 2 ml of heptane and 7.5 ml of hexene-1 were introduced. The pressure of the hydrogen-carbon monoxide mixture (1/1 molar) was brought to 2 MPa, the temperature was increased to 80° C. and stirring was commenced. After 5 hours, stirring was stopped and the reaction mixture was allowed to cool and decant, then the pressure was released. After extraction from the autoclave, the upper organic phase was slightly colored. The hexene-1 conversion was 48% by weight. The selectivity for C7 aldehydes was 60% and the n/iso (n-heptanal/isoheptanals) ratio was 2.4.

EXAMPLE 12

The hydroformylation reaction was carried out in the same apparatus and using the same operating procedure as that described in Example 1. 19.3 mg of rhodium-dicarbonyl acetylacetonate, 18.3 mg of 2,2'-bipyridyl-4,4'-dicarboxylic acid, 4 ml of butyl-methyl-midazolium tetrafluoroborate, 2 ml of heptane and 7.5 ml of hexene-1 were introduced. The pressure of the hydrogen-carbon monoxide mixture (1/1 molar) was brought to 2 MPa, the temperature was increased to 80° C. and stirring was commenced. After 5 hours, stirring was stopped and the reaction mixture was allowed to cool and decant, then the pressure was released. After extraction from the autoclave, the upper organic phase was slightly colored. The hexene-1 conversion was 75% by weight. The selectivity for C7 aldehydes was 66% and the n/iso (n-heptanal/isoheptanals) ratio was 1.2.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process comprising conducting a hydroformylation reaction of olefinically unsaturated compounds in the liquid phase in which the reaction is carried out in the presence of at least one complex of at least one of cobalt and rhodium co-ordinated by at least one nitrogen-containing ligand, and at least one non-aqueous ionic solvent comprising at least one organic-inorganic salt with general formula $Q^+A^-$, where $Q^+$ represents at least one quaternary radical selected from the group consisting of quaternary ammonium and quaternary phosphonium, and $A^-$ represents an anion, with the provision that said at least one ligand is devoid of tertiary phosphines, stibines, arsines and phosphites.

2. A process according to claim 1, wherein said at least one complex of at least one of cobalt and rhodium is formed from a precursor selected from the group consisting of cobalt and rhodium salts and carbonyl complexes.

3. A process according to claim 1, wherein said at least one complex is formed from an acetylacetonate, carboxylate, dicobalt-octacarbonyl, cobalt-tetracarbonyl hydride, rhodium-dicarbonyl acetyl-acetonate or carbonyl cluster.

4. A process according to claim 1, wherein the nitrogen-containing ligand is selected from the group consisting of monoamines, di-, tri- and polyamines, imines, diimines, pyridine and substituted pyridines, bipyridine, imidazole and substituted imidazoles, pyrrole and substituted pyrroles and pyrazole and substituted pyrazoles.

5. A process according to claim 4, wherein the nitrogen-containing ligand is pyridine or a substituted pyridine.

6. A process according to claim 4, wherein the nitrogen-containing ligand is imidazole or a substituted imidazole.

7. A process according to claim 4, wherein the nitrogen-containing ligand is an imine or a diimine.

8. A process according to claim 1, wherein the non-aqueous ionic solvent is selected from the group consisting of liquid salts with general formula $Q^+A^-$ where $Q^+$ represents quaternary ammonium and/or quaternary phosphonium and $A^-$ represents any anion which can form a liquid salt at below 90° C.

9. A process according to claim 8, wherein $A^-$ is an acetate, halogenoacetate, tetrafluoroborate, tetrachloroborate, hexafluorophosphate, hexafluoroantimonate, fluorosulfonate, perfluoroalkylsulfonate, bis-(perfluoroalkylsulfonyl)amide or arene-sulfonate ion.

10. A process according to claim 8 wherein the quaternary radical is of the formula $NR^1R^2R^3R^{4+}$, $P R^1R^2R^3R^{4+}$, $R^1R^2N=C R^3R^{4+}$, or $R^1R^2P=C R^3R^{4+}$, where $R^1, R^2, R^3$, and $R^4$, which may be identical or different, represent hydrogen with the exception of the $NH_4^+$ cation for $NR^1R^2R^3R^{4+}$, or hydrocarbyl residues containing 1 to 12 carbon atoms.

11. A process according to claim 8 is a derivative of at least one of nitrogen-containing and phosphorus-containing heterocycle containing 1,2 or 3 nitrogen and/or phosphorus atoms, in which the cycles are constituted by 4 to 10 atoms.

12. A process according to claim 8, wherein the quaternary radical is at least one cation selected from the group consisting of:

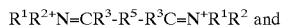
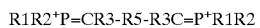

where R1, R2 and R3, which may be identical or different, are defined as in claim 10, and R5 represents an alkylene or phenylene residue.

13. A process according to claim 8, wherein the quaternary radical is selected from the group consisting of N-butylpyridinium, N-ethylpyridinium, 3-ethyl-1-methylimidazolium, 3-butyl-1-methyl-imidazolium, diethylpyrazolium, pyridinium, trimethylphenyl ammonium and tetrabutyl-phosphonium.

14. A process according to claim 8, wherein the non-aqueous ionic solvent is selected from the group consisting of N-butylpyridnium hexafluorophosphate, N-ethylpyridinium tetrafluoroborate, tetrabutylphosphonium tetra-fluoroborate, 3-butyl-1-methylimidazolium tetrafluoroborate, 3-butyl-1-methylimidazolium hexafluoroantimonate, 3-butyl-1-methylimidazolium hexafluorophosphate, 3-butyl-1-methyl-imidazolium trifluoromethylsulfonate, pyridinium fluorosulfonate and trimethylphenyl-ammonium hexafluorophosphate.

15. A process according to claim 1, wherein the concentration of cobalt and/or rhodium complex in the liquid ionic solvent is in the range of 0.1 to 5 moles per liter, and the mole ratio between the nitrogen-containing ligand and the cobalt and/or rhodium part of the coordinated complex is in the range of 0.1 to 100.

16. A process according to claim 1, wherein the olefinically unsaturated compounds are selected from the group formed by monoolefins, diolefins, and olefinic compounds comprising one or more heteroatoms.

17. A process according to claim 1, wherein the hydroformylation reaction is carried out with the ratio of partial pressures of hydrogen to carbon monoxide of 10:1 to 1:10, at a temperature in the range 30° C. to 200° C., with a pressure in the range 1 MPa to 20 MPa.

18. A process according to claim 10, wherein only one of $R^1, R^2, R^3$ and $R^4$ represents hydrogen.

19. A process according to claim 11, wherein the heterocycles contain 5 or 6 atoms.

20. A process according to claim 16, wherein at least one heteroatom is in the form of a ketone or carboxylic acid function.

21. A process according to claim 16, wherein the olefinically unsaturated olefins are conjugated diolefins.

22. A process comprising conducting a hydroformylation reaction of olefinically unsaturated compounds in the liquid phase in which the reaction is carried out in the presence of at least one complex of at least one of cobalt and rhodium coordinated by at least one ligand selected from the group consisting of pyridine and substituted pyridine, imidazole and substituted imidazole, an imine and a diimine, and at least one non-aqueous ionic solvent comprising at least one organic-inorganic salt with general formula $Q^+A^-$, where $Q^+$ represents at least one quaternary radical selected from the group consisting of quaternary ammonium and quaternary phosphonium, and $A^-$ represents an anion.

23. A process according to claim 22, wherein the nitrogen-containing ligand is pyridine or a substituted pyridine.

24. A process according to claim 22, wherein the nitrogen-containing ligand is imidazole or a substituted imidazole.

25. A process according to claim 22, wherein the nitrogen-containing ligand is an imine or a diimine.

26. A process comprising conducting a hydroformylation reaction of olefinically unsaturated compounds in the liquid phase in which the reaction is carried out in the presence of at least one complex of at least one of cobalt and rhodium co-ordinated by at least one ligand, said ligand being a compound consisting of carbon, nitrogen, hydrogen and optionally at least one of oxygen and sulfur, and at least one non-aqueous ionic solvent comprising at least one of organic-inorganic salt with general formula $Q^+A^-$, where $Q^+$ represents at least one quaternary radical selected from the group consisting of quaternary ammonium quaternary phosphonium, and $A^-$ represents an inion.

27. A process according to claim 26, wherein all ligands consist of carbon, nitrogen, hydrogen and optionally at least one of oxygen and sulfur.

* * * * *

UNITED STATES PATENT AND TRADEMARK OFFICE
CERTIFICATE OF CORRECTION

PATENT NO.    : 6,469,216 B2
DATED         : October 22, 2002
INVENTOR(S)   : Hillebrand et al.

It is certified that error appears in the above-identified patent and that said Letters Patent is hereby corrected as shown below:

Column 9,
Line 31, change "Q$^-$" to -- Q$^+$ --.
Line 56, should read -- $R^1R^{2+}P=CR^3-R^5-R^3C=P^+R^1R^2$ --.
Line 57, change "R1, R2 and R3" to -- $R^1$, $R^2$ and $R^3$ --.
Line 58, delete "are defined as in claim 10," and insert -- represent hydrogen or a hydrocarbon residue containing 1 to 12 carbon atoms, --.

Signed and Sealed this

Nineteenth Day of August, 2003

JAMES E. ROGAN
*Director of the United States Patent and Trademark Office*